(12) United States Patent
Kadykowski et al.

(10) Patent No.: US 10,117,700 B2
(45) Date of Patent: Nov. 6, 2018

(54) ENDOSCOPIC VESSEL HARVESTER WITH BLUNT AND ACTIVE RING DISSECTION

(71) Applicant: TERUMO CARDIOVASCULAR SYSTEMS CORPORATION, Ann Arbor, MI (US)

(72) Inventors: Randal J. Kadykowski, South Lyon, MI (US); Kevin R. Line, Ann Arbor, MI (US)

(73) Assignee: TERUMO CARDIOVASCULAR SYSTEMS CORPORATION, Ann Arbor, MI (US)

( * ) Notice: Subject to any disclaimer, the term of this patent is extended or adjusted under 35 U.S.C. 154(b) by 323 days.

(21) Appl. No.: 15/070,344

(22) Filed: Mar. 15, 2016

(65) Prior Publication Data

US 2017/0035487 A1  Feb. 9, 2017

Related U.S. Application Data

(60) Provisional application No. 62/201,345, filed on Aug. 5, 2015, provisional application No. 62/201,338, filed on Aug. 5, 2015.

(51) Int. Cl.
*A61B 18/08* (2006.01)
*A61B 18/04* (2006.01)
(Continued)

(52) U.S. Cl.
CPC ............ *A61B 18/082* (2013.01); *A61B 18/04* (2013.01); *A61B 17/32* (2013.01); *A61B 17/320016* (2013.01); *A61B 18/14* (2013.01); *A61B 18/1402* (2013.01); *A61B 2017/00013* (2013.01); *A61B 2017/00969* (2013.01);
(Continued)

(58) Field of Classification Search
CPC ........ A61B 18/082; A61B 2017/00969; A61B 2018/00404; A61B 2018/00595; A61B 2017/320044
See application file for complete search history.

(56) References Cited

U.S. PATENT DOCUMENTS 5,013,312 A  5/1991  Parins et al.
5,980,549 A  11/1999  Chin
(Continued)

*Primary Examiner* — Ronald Hupczey, Jr.
*Assistant Examiner* — Rachel A Vierra
(74) *Attorney, Agent, or Firm* — Darryl Newell; MacMillan, Sobanski & Todd, LLC

(57) ABSTRACT

A vessel dissector for harvesting a target vessel has a tubular member carrying a blunt transparent tip with a terminus for blunt dissection of tissue and a base affixed to the tubular member. An active ring set has first and second ring segments mounted to distal ends of respective manipulator bars in the tubular member. The ring segments juxtapose to define a closed loop with an inner diameter larger than the outside diameter of the tip base. The ring segments are movable between a retracted position nested at the base and respective extended positions distally forward of the terminus. At least one of the ring segments is energizable to cut and cauterize a cylindrical pedicle including the target vessel. The ring segments independently extend longitudinally to provide a variable gap between the ring segments to capture, cut, and cauterize side branches to the target vessel between the ring segments.

7 Claims, 5 Drawing Sheets

(51) Int. Cl.
  *A61B 18/00* (2006.01)
  *A61B 17/00* (2006.01)
  *A61B 17/32* (2006.01)
  *A61B 17/06* (2006.01)
  *A61B 18/14* (2006.01)

(52) U.S. Cl.
  CPC .............. *A61B 2017/06085* (2013.01); *A61B 2017/320004* (2013.01); *A61B 2017/32004* (2013.01); *A61B 2017/320044* (2013.01); *A61B 2017/320093* (2017.08); *A61B 2017/320095* (2017.08); *A61B 2018/00184* (2013.01); *A61B 2018/00404* (2013.01); *A61B 2018/00595* (2013.01); *A61B 2018/00601* (2013.01); *A61B 2018/00982* (2013.01)

(56) References Cited

U.S. PATENT DOCUMENTS

| | | | |
|---|---|---|---|
| 6,129,661 A | 10/2000 | Iafrati et al. | |
| 6,309,400 B2 | 10/2001 | Beaupre | |
| 6,527,771 B1 * | 3/2003 | Weadock | A61B 17/00008 606/170 |
| 7,077,803 B2 | 7/2006 | Kasahara et al. | |
| 7,331,971 B2 | 2/2008 | Kasahara et al. | |
| 7,510,562 B2 * | 3/2009 | Lindsay | A61B 17/00008 606/159 |
| 7,556,633 B2 | 7/2009 | Lindsay | |
| 7,909,762 B2 | 3/2011 | Usher et al. | |
| 7,942,891 B2 | 5/2011 | Genovesi et al. | |
| 7,981,133 B2 | 7/2011 | Chin | |
| 8,097,010 B2 | 1/2012 | Kasahara et al. | |
| 8,292,879 B2 * | 10/2012 | Manwaring | A61B 18/082 606/27 |
| 8,372,066 B2 | 2/2013 | Manwaring et al. | |
| 8,372,096 B2 | 2/2013 | Kadykowski et al. | |
| 8,377,052 B2 | 2/2013 | Manwaring et al. | |
| 8,414,569 B2 | 4/2013 | Manwaring et al. | |
| 8,419,724 B2 | 4/2013 | Manwaring et al. | |
| 8,425,503 B2 | 4/2013 | Manwaring et al. | |
| 8,430,870 B2 | 4/2013 | Manwaring et al. | |
| 8,430,898 B2 | 4/2013 | Wiener et al. | |
| 8,491,578 B2 | 7/2013 | Manwaring et al. | |
| 8,523,850 B2 | 9/2013 | Manwaring et al. | |
| 8,523,851 B2 | 9/2013 | Manwaring et al. | |
| 8,523,852 B2 | 9/2013 | Manwaring et al. | |
| 8,617,151 B2 | 12/2013 | Denis et al. | |
| 8,858,544 B2 | 10/2014 | McNally et al. | |
| 8,915,909 B2 | 12/2014 | Manwaring et al. | |
| 8,932,279 B2 | 1/2015 | Stringham et al. | |
| 9,078,655 B2 | 7/2015 | Manwaringt et al. | |
| 2008/0208192 A1 | 8/2008 | Kadykowski et al. | |
| 2008/0255407 A1 | 10/2008 | Blakeney et al. | |
| 2010/0292533 A1 | 11/2010 | Kasahara et al. | |
| 2013/0165746 A1 * | 6/2013 | Chin | A61B 17/285 600/36 |
| 2015/0073207 A1 | 3/2015 | Langford | |

* cited by examiner

ENDOSCOPIC VESSEL HARVESTER WITH BLUNT AND ACTIVE RING DISSECTION

CROSS REFERENCE TO RELATED APPLICATIONS

This application claims priority to U.S. provisional application 62/201,345, filed on Aug. 5, 2015, entitled "Vessel Dissector and Harvester," and to U.S. provisional application 62/201,338, filed on Aug. 5, 2015, entitled "Vessel Cauterizing Ring," both of which are hereby incorporated by reference in their entirety.

STATEMENT REGARDING FEDERALLY SPONSORED RESEARCH

Not Applicable.

BACKGROUND OF THE INVENTION

The present invention relates in general to harvesting of living vessels for use in grafting, and, more specifically, to a harvesting device for endoscopically removing a vessel and a surrounding pedicle of fat and connective tissue wherein the device is capable of both blunt dissection and active cutting.

Blood vessels are often dissected from one portion of a living body to be implanted in another portion of the body by a surgical procedure, such as in a coronary artery bypass graft (CABG) or other cardiovascular procedure. An artery or vein is "harvested" (i.e., removed) from its natural location in a patient's body and reconnected to provide blood circulation elsewhere in the body. Among the preferred sources for the vessels to be used as the bypass graft are the saphenous vein in the leg and the radial artery in the arm.

Endoscopic surgical procedures for harvesting a section of a blood vessel (e.g., the saphenous vein) subcutaneously have been developed in order to avoid disadvantages and potential complications of harvesting of the blood vessel by exposing the desired vein section externally through a continuous incision along the leg. The continuous incision for exposing the vein and for introducing the surgical instruments to seal and sever adjoining tissue and side branches of the vessel results in a significant healing process and associated risks.

The known minimally-invasive endoscopic techniques employ a small incision for locating the desired vessel and for introducing one or more endoscopic devices into the small incision. For example, typical commercially available products for performing the endoscopic blood vessel harvesting procedure include a number of separate endoscopic devices that are each inserted into the patient. These endoscopic devices include, for example, an insufflation mechanism having plastic tubing to supply air or $CO_2$ to insufflate the subcutaneous area; an endoscope having a camera and light cables in order to visualize both the dissection and harvesting procedures; a dissector mechanism to dissect or separate the vessel from connective tissues in the body (i.e., blunt dissection); and a cutting mechanism to sever and seal any side branches from the vessel and then remove the vessel from the body (i.e., active cutting). In certain instances, the combination of mechanisms can be bulky and cumbersome for the clinician performing the vessel harvesting. Also, in certain instances, these mechanisms require that a relatively large diameter wound and cavity be formed within the patient in order to accommodate all the separate mechanisms.

Existing harvesting devices have required an intricate and physically demanding procedure to isolate a vessel from surrounding tissue and to cut and coagulate side branches. This required a high level of skill and practice for the person performing the harvesting procedure. Even with good expertise, several potential sources of damage to the harvested vessel remain. Harvesting typically requires multiple passes of one or more separate devices resulting in much contact with the vessel, potentially leading to endothelial damage. To create a sufficient working space and to allow visualization for tissue separation and side branch cutting, significant insufflation is often used. The $CO_2$ insufflation gas can lead to tissue acidosis, $CO_2$ embolism, and other complications. The common use of electrocauterization for cutting and coagulating the side branches can result in thermal spreading to the harvested vessel and sometimes also results in side branch stubs that are too short for obtaining a good, leak-proof seal.

It has been discovered that improved patency can be obtained for a vein graft if some surrounding tissue is left intact around the desired vessel. To address the absence of endoscopic devices capable of maintaining a layer of surrounding tissue (i.e., a pedicle) over the harvested vessel, co-pending U.S. application Ser. No. 14/021,537, filed Sep. 9, 2013, entitled "Single-Pass Endoscopic Vessel Harvesting" discloses a ring-shaped blade mounted to a sheath and disposed in a plane substantially perpendicular to the longitudinal direction and proximal of a dissector tip. The blade forms a lateral loop to encircle the vessel from the flanking tunnel and to make a vasiform cut including a pedicle around the vessel as the sheath advances. The disclosure of application Ser. No. 14/021,537 is incorporated herein by reference.

To reduce some disadvantages that may be associated with electrocauterization or other cutting methods, ferromagnetic heating can be used on a cutting surface to generate a controlled heating, as shown in co-pending U.S. application Ser. No. 14/926,305, filed Oct. 29, 2015, entitled "Single-Pass Endoscopic Vessel Harvesting" which is also incorporated herein by reference. Appropriate ferromagnetic materials and the generation of energizing signals can be as disclosed in U.S. Pat. No. 8,292,879.

The dissection of a vessel and the surrounding pedicle requires the cutting and/or separating of various tissue structures with a variety of physical properties, all done in a small working space. Even when using active cutting to harvest both the target vessel and a surrounding pedicle, there remains a need for blunt dissection (e.g., to create the working space or for exposing a side branch or a portion of the target vessel for active cutting). Thus, a device capable of both blunt dissection and active cutting is desirable.

SUMMARY OF THE INVENTION

In one aspect of the invention, a vessel dissector is provided for harvesting a target vessel from a donor site. A tubular member extends longitudinally between proximal and distal ends. A blunt transparent tip has a terminus for blunt dissection of tissue at the donor site and a base affixed to the distal end of the tubular member with a predetermined outside diameter. An active ring set has first and second ring segments mounted to distal ends of respective manipulator bars mounted in the tubular member for relative movement. The ring segments juxtapose to define a closed loop with an inner diameter larger than the predetermined outside diameter of the tip base. The ring segments are movable between a retracted position nested at the base and respective extended positions distally forward of the terminus. At least one of the ring segments is energizable to cut and cauterize a cylindrical pedicle from the tissue at the donor site including the target vessel. The ring segments independently extend longitudinally to provide a variable gap between the ring segments to capture, cut, and cauterize side branches to the target vessel between the ring segments.

DETAILED DESCRIPTION OF PREFERRED EMBODIMENTS

Figure 1:
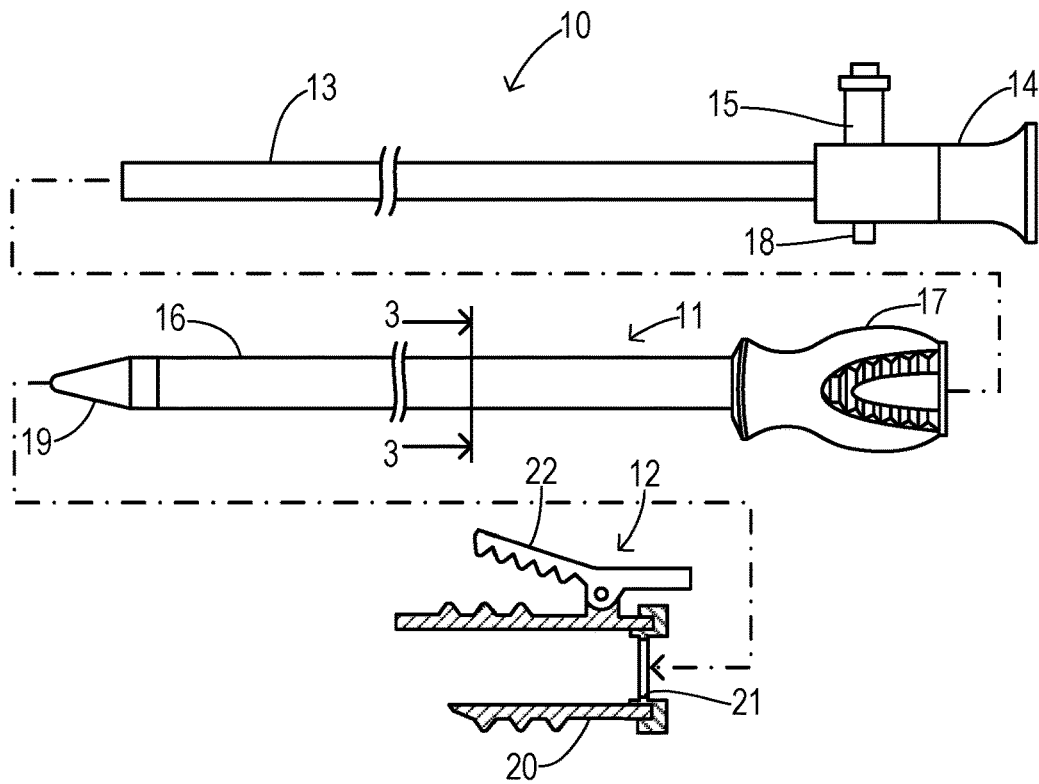
FIG. 1 is a plan view of a prior art blunt dissector with an endoscope and a trocar.

A vessel harvesting system shown in FIG. 1 includes an endoscope 10 to perform observation in a body, a dissector apparatus 11 to dissect a blood vessel in the body, and a trocar 12 to help insert the endoscope 10 and dissector apparatus 11 into the body. Endoscope 10 is a rigid endoscope and includes an elongated rod-like inserting portion 13. The proximal end of inserting portion 13 connects to an end adapter 14 to transmit an endoscopic image. A light guide port 15 projects from end adapter 14. Light guide port 15 connects to a light guide cable to supply illumination light to the endoscope 10.

Dissector apparatus 11 includes a tubular main body portion 16 comprising a hollow longitudinal rod within which endoscope 10 is to be inserted. Endoscope 10 is inserted or removed from longitudinal rod 16 through a handle portion 17. Endoscope 10 may be secured inside dissector 11 by a small nub 18, found opposite light guide port 15 on end adapter 14 of endoscope 10 and held by a conventional mechanism found inside handle portion 17.

The material of longitudinal rod 16 material is selected from fluoropolymers, which are well known materials. Examples of fluoropolymers include polymers such as polytetrafluoroethylene (PTFE commonly referred to as Teflon), perfluoroalkoxy (PFA), fluorinated ethylene propylene (FEP), polyvinylidene fluoride (PVDF), ethylene-tetrafluoroethylene (ETFE), ethylene-chlorotrifluoroethylene (ECTFE), and mixtures of fluoropolymers such as MFA or THV, or mixtures of any of the foregoing. The most preferred material for constituting the outer surface of longitudinal rod 16 is PTFE. The use of a fluoropolymer reduces the friction caused by moving rod 16 through connective tissue, thereby reducing the force required to perform a dissection.

A blunt dissector tip 19 is disposed at the distal end of longitudinal rod 16. Tip 19 has a conical shape and comprises a transparent synthetic resin material to facilitate viewing through tip 19 using endoscope 10. Trocar 12 includes a body 20 to guide dissector apparatus 11 into the incision site. An aperture seal 21 is located on the surface of the proximal end of body 20. Aperture seal 21 allows dissector 11 to be inserted in body 20 of trocar 12 in one fluid forward motion. The outer surface of trocar body 20 includes a projection to engage with living tissue and a holding portion 22 to hold the body 20 onto the living tissue.

To conduct the harvesting of a vessel, an incision may be made in the vicinity of a knee or a wrist immediately above a target blood vessel to be harvested. Body 20 of trocar 12 is inserted in the incision and held by holding portion 22 with respect to the incision. Endoscope 10 is inserted in dissector apparatus 11. Light guide connector 15 of endoscope 10 is inserted in dissector 11. Small nub 18 located on the bottom portion of endoscope 10 engages a mechanism in handle 17 to lock them. The distal end of endoscope 10 is caused to project from the distal end of longitudinal rod 16 into tip 18 for providing a view through tip 18. Endoscope 10 and dissector 11 are then inserted into the body through trocar 12 in one forward movement.

Figure 2:
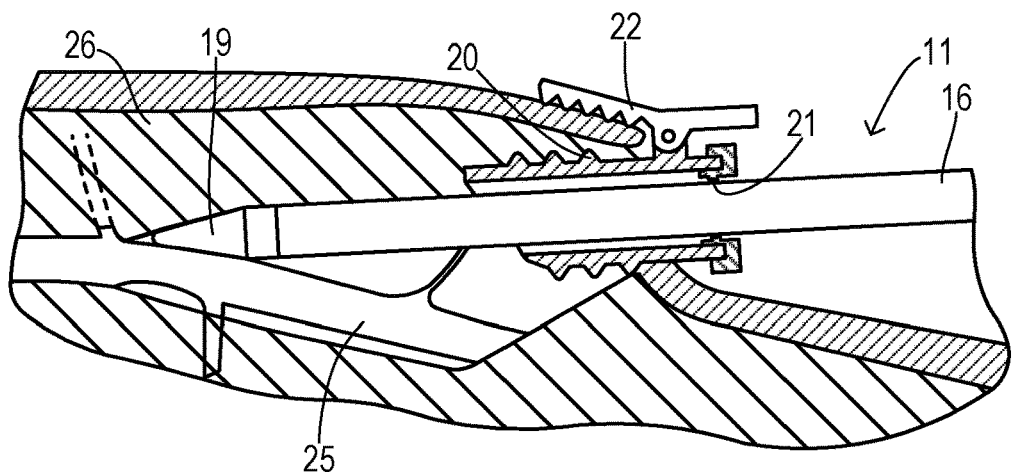
FIG. 2 is a partial cross section showing a dissector inserted into a patient's body and guided by a trocar.

FIG. 2 shows dissector 11 inserted in the body to dissects a portion of a target vessel 25 from connective tissue 26. Blunt tip 19 is adapted to penetrate connective tissue to open a space at or around vessel 25, for example. However, tip 19 in this conventional device is not adapted to create a vasiform cut, to dissect a pedicle surrounding vessel 25, or to otherwise cut or cauterize vessel 25 or any of its side branches.

Figure 3:
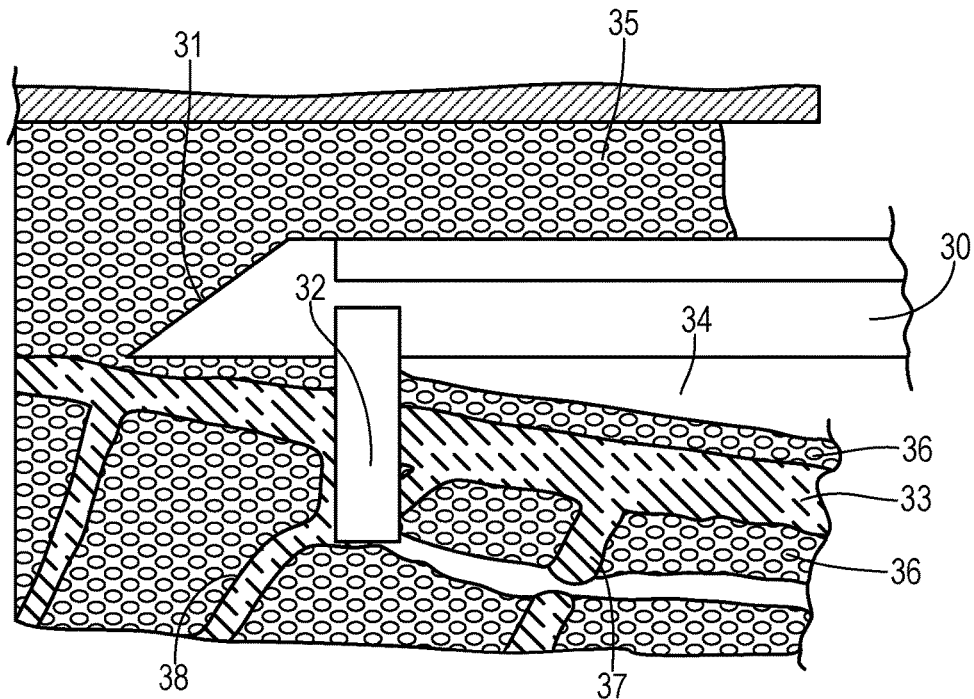
FIG. 3 is a longitudinal cross section showing the active harvesting of a vessel with a surrounding pedicle using an active ring to make a vasiform cut.

FIG. 3 shows a side view of a vessel dissector 30 during the formation of a vasiform cut around a target vessel 33. Dissector 30 includes a blunt tip 31 and a ring blade 32, wherein tip 31 penetrates tissue spaced away from vessel 33 to form a flanking tunnel 34. As an operator advances tip 31 above target vessel 33 so as to maintain an amount of connective tissue 35 between tip 31 and vessel 33, ring blade 32 is energized in order to make a vasiform cut which simultaneously excises pedicle 36 and vessel 33 while automatically severing and cauterizing side branches such as branches 37 and 38. Preferably, ring blade 32 is comprised of a conductor forming a loop which is connected to a signal generator (not shown) via a lead-in section. To provide induction heating for cutting and cauterizing at its edge, appropriate regions of ring blade 32 are coated with a ferromagnetic material (e.g., an alloy coating applied circumferentially over a section of the wire along one of its passes within the loop).

Figure 4:
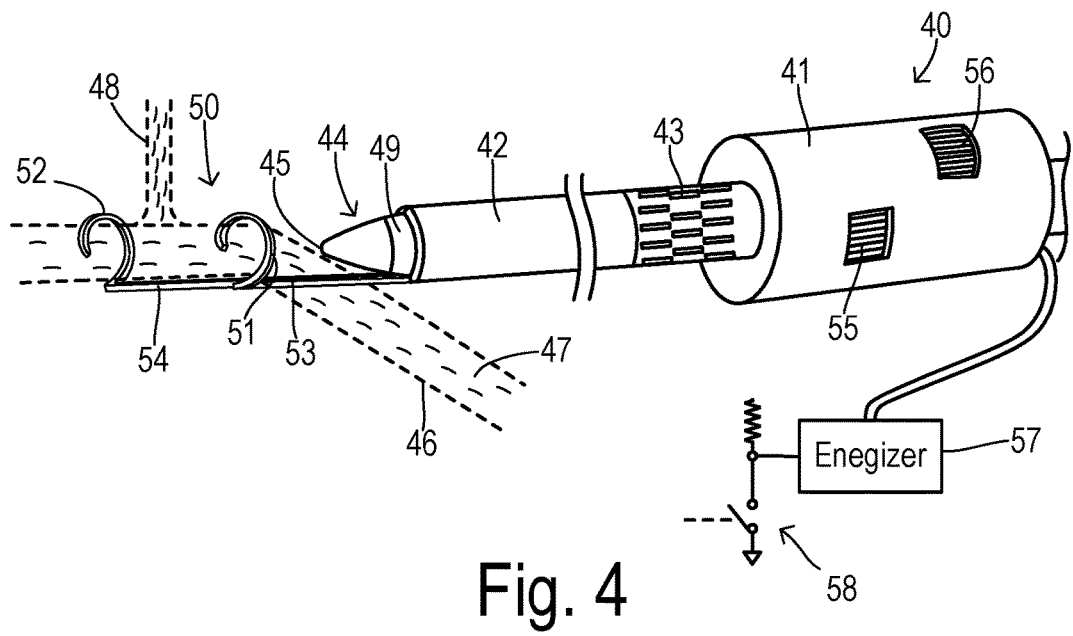
FIG. 4 is a side view of a combined blunt/active dissector with an active ring set in an extended position at one end and a handle at the other end.

FIG. 4 shows a first embodiment of a blunt/active dissector instrument 40 with a handle 41 supporting a tubular body member (i.e., sheath) 42 having a hand grip 43 (e.g., a rubberized coating) at its proximal end mounted to handle 41 and having a tip 44 mounted to its distal end. Tip 44 has a blunt point at a terminus 45 for performing blunt dissection. In the present invention, tip 44 may be used to penetrate or separate tissue around a pedicle 46 being excised around a target vessel 47, for example. In order to cut and cauterize side branches such as a side branch 48 and/or other connective tissues, an active ring set 50 is provided which includes ring segments 51 and 52 at the ends of respective manipulator bars 53 and 54. Bars 53 and 54 are shown having an approximately rectangular cross section, but could alternatively be comprised of cylindrical rods (e.g., steel) or have other cross sections. Handle 41 includes ring rod actuators 55 and 56 which is a known type of mechanism for enabling a user to manually extend ring segments 51 and 52 independently between extended positions shown in FIG. 4 and retracted positions nested against tip 44. Guide slots or other abutments (not shown) may be provided within hollow body member 42 and/or tip 44 to maintain bars 53 and 54 in alignment.

Tip 44 has a base section 49 proximate to the distal end of tubular member 42. Base 49 provides a predetermined outside diameter which is selected to receive ring segments 51 and 52 when they are retracted. Thus, ring segments 51 and 52 may be nested at base 49 to facilitate use of tip 44 and terminus 45 in blunt dissection of tissue that the donor site for the target vessel. The outside diameter of base 49 may be stepped down from the outside diameter of body member 42 by an amount sufficient to accommodate the radial thickness of ring segments 51 and 52 to aid in smooth sliding of body member 42 within the body cavity during blunt dissection.

Ring segments 51 and 52 form overlapping partial rings. When the overlapping rings are juxtaposed with each other they define a closed loop with an inner diameter larger than the predetermined outside diameter of base 49. Offset openings in segments 51 and 52 provide an opening for inserting the vessel/pedicle into the ring for dissection. At least one of ring segments 51 and 52 has an active cutting surface, and preferably both segments 51 and 52 have active cutting surfaces so that together they provide a continuous cutting (vasiform) loop for dissecting the desired pedicle during active dissection.

By extending bars 53 and 54 using ring rod actuators 55 and 56, ring segments 51 and 52 are placed in longitudinally extended positions distally forward of terminus 45. Ring segments 51 and 52 may be independently positioned to provide a variable gap between ring segments 51 and 52. When ring segments 51 and 52 are touching or close together, they may be advanced through tissue in order to make the vasiform cut to dissect a pedicle around target vessel 47 by energizing an active cutting surface such as a ferromagnetic heating surface or an ultrasonic surface. The active cutting surface may be energized by a signal generator or energizer 57 which is turned on and off by a manual push button switch 58, for example. In a preferred embodiment, ferromagnetic heating is used in ring segments 51 and 52 by providing a ferromagnetic coating at strategic locations over a signal conductor that passes through each manipulator bar 53 and 54 and follows a loop around ring segments 51 and 52.

Figure 5:
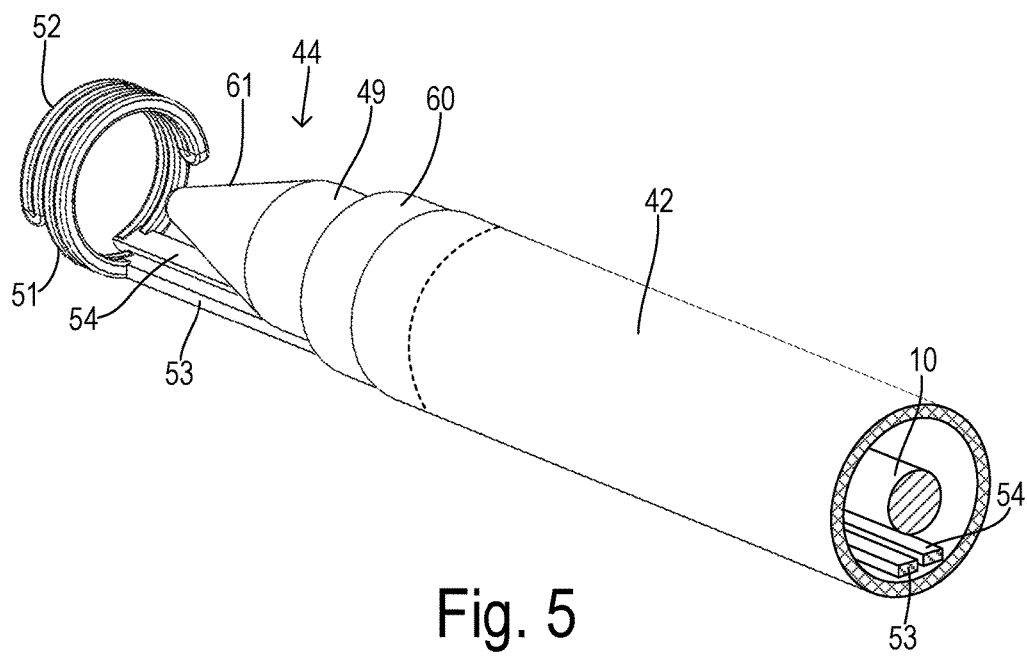
FIG. 5 is a rear perspective view of a distal tip of a dissector of the invention with the ring set extended together.

FIGS. 5-9 show the distal end of device 40 in greater detail with ring segments 51 and 52 in various positions. In FIG. 5, ring segments 51 and 52 are extended together while remaining in abutment to present a continuous ring adapted for making the vasiform cut. Each ring segment 51 and 52 comprises a looping conductor extending from one its manipulator bar, to the remote end of the segment, and returning to the respective manipulator bar. Each looping conductor is electrically connected to the signal generator by respective conductor paths within the manipulator bars. Ferromagnetic heating material is used to form contact surfaces, preferably at a forward (distal) surface of forward ring segment 52 and on at least one of the adjoining surfaces of ring segments 51 and 52. The forward surface of ring segment 52 would be adapted to cut and cauterize tissue while penetrating forward into the tissue in order to form a cylindrical cut around the target vessel and pedicle. The internal, adjoining surfaces would be adapted to cutting side branches that can be maneuvered into a gap between the ring segments.

Figure 6:
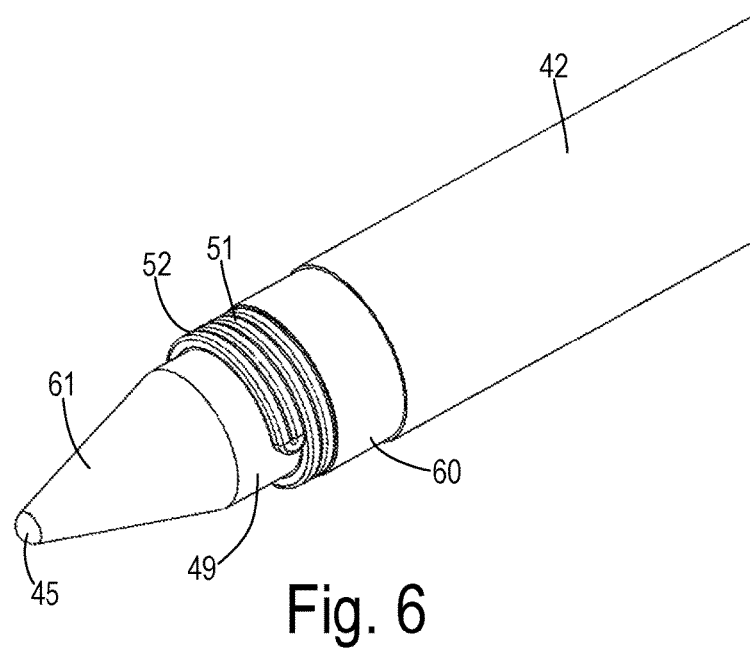
FIG. 6 is a front perspective view of the distal tip of the dissector of FIG. 5 with the ring set retracted.

Base section 49 of tip 44 provides a landing region between a slope section 61 and a mounting collar 60 which is bonded to an inner surface of tubular body member 42. FIG. 6 shows ring segments 51 and 52 retracted onto base section 49 to provide a nested configuration adapted for performing a blunt dissection.

Figure 7:
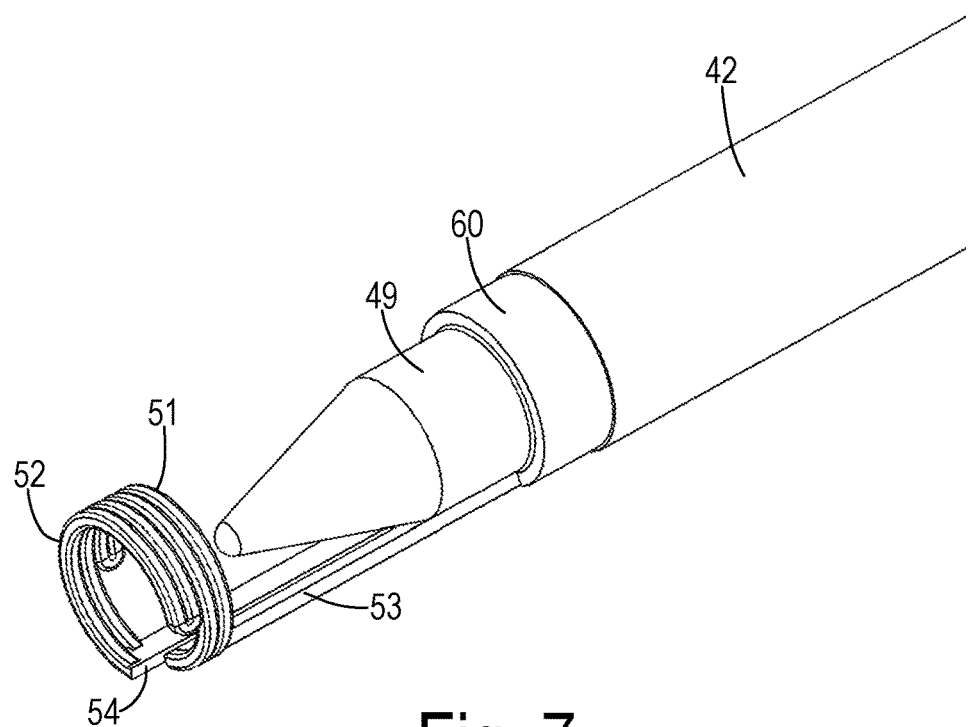
FIG. 7 is a front perspective view of the distal tip of the dissector of FIG. 5 with the ring set extended together.
Figure 8:
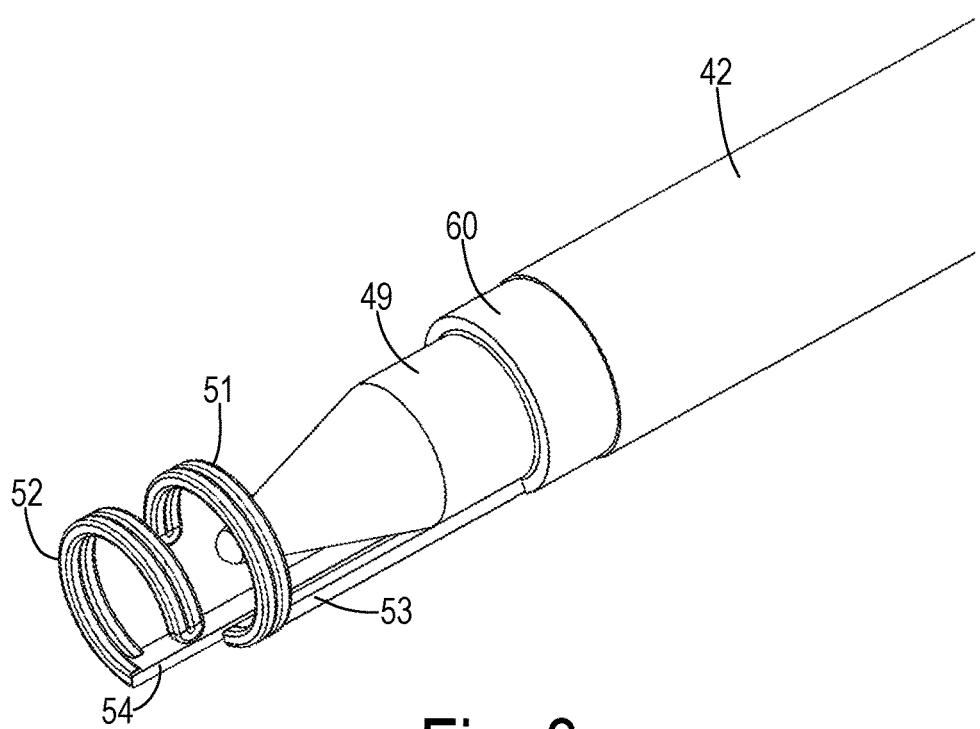
FIG. 8 is a front perspective view of the distal tip of the dissector of FIG. 5 with the ring set extended by different distances.

FIGS. 7 and 8 show extended positions for active dissection which cuts and cauterizes tissue. Ring segments 51 and 52 are in contact with each other in FIG. 7, wherein segments 51 and 52 may cooperate to cut a cylindrical section through tissue at a donor site for the target vessel and surrounding pedicle. They are extended by different amounts in FIG. 8 to form a gap between them, wherein the gap size is manually controlled to permit segments 51 and 52 to be spread apart and then brought back together in order to cut/cauterize tissue between the ring segments while under compression. During dissection, the blunt dissection configuration can be used to expose a side branch. Then active cutting can be used to sever and cauterize the side branch by extending ring segments 51 and 52 with a gap sufficient to capture the side branch, and then closing the gap to pinch the side branch between the ring segments and energizing the ferromagnetic heater to cut and cauterize the branch.

Figure 9:
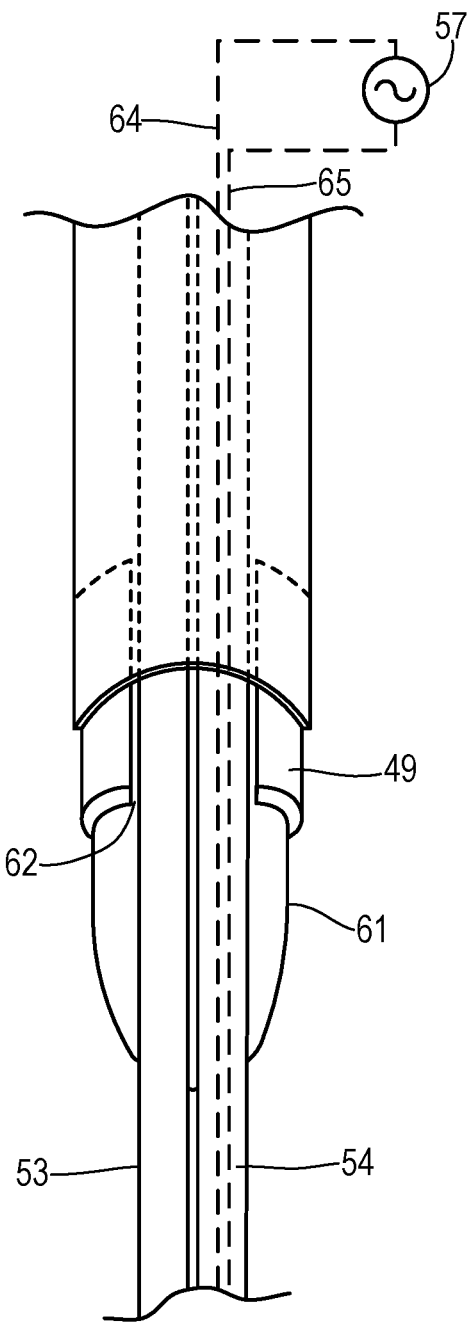
FIG. 9 is a bottom view of the distal tip of the dissector of FIG. 5 with the ring set extended.

FIG. 9 is a bottom view showing a recess 62 in base section 49 that receives manipulator bars 53 and 54. A resilient seal (not shown) can be disposed within recess 62 and/or on tubular body member 42 to reduce ingress of fluids into the device. Conductive signal lines 64 and 65 may be embedded in bar 54 to carry the energization signal to initiate ferromagnetic heating, for example.

What is claimed is:
1. A vessel dissector for harvesting a target vessel from a donor site, comprising:
  a tubular member extending longitudinally between proximal and distal ends;
  a blunt transparent tip having a terminus for blunt dissection of tissue at the donor site and a base affixed to the distal end of the tubular member with a predetermined outside diameter; and
  an active ring set having first and second ring segments mounted to distal ends of respective manipulator bars extending through the tubular member for relative movement;
  wherein the ring segments juxtapose to define a closed loop with an inner diameter larger than the predetermined outside diameter of the tip base;
  wherein the ring segments are movable between a retracted position nested at the base and respective extended positions distally forward of the terminus;
  wherein the first and second ring segments each comprises a partial ring, wherein the partial rings have offset openings configured to receive a cylindrical pedicle containing the target vessel into the ring segments when they are longitudinally extended by different amounts;
  wherein at least one of the ring segments is energizable to cut and cauterize the cylindrical pedicle and target vessel from the tissue at the donor site after the ring segments are juxtaposed to provide the closed loop; and
  wherein the ring segments independently extend longitudinally to provide a variable gap between the ring segments to capture, cut, and cauterize side branches of the target vessel between the ring segments.

2. The vessel dissector of claim 1 wherein the at least one energizable ring segment is comprised of a ferromagnetic heating body arranged to directly contact the tissue, and wherein the respective manipulator bar includes conductive lines for carrying an energization signal to the ferromagnetic heating body.

3. The vessel dissector of claim 1 wherein the first and second ring segments are each comprised of a respective ferromagnetic heating body arranged to directly contact the tissue.

4. The vessel dissector of claim 1 further comprising:
a handle mounted to the proximal end of the tubular member; and
first and second ring rod actuators disposed in the handle and coupled to the manipulator bars to manually control movement of the ring segments.

5. The vessel dissector of claim 4 wherein the ring rod actuators move the manipulator bars longitudinally.

6. The vessel dissector of claim 1 wherein the blunt tip includes a recess slidably receiving the manipulator bars.

7. The vessel dissector of claim 1 further comprising an endoscope extending through the tubular member into the blunt tip.

\* \* \* \* \*